United States Patent [19]

Casey et al.

[11] Patent Number: 4,781,183
[45] Date of Patent: Nov. 1, 1988

[54] SURGICAL PROSTHESIS

[75] Inventors: Donald J. Casey, Ridgefield; Peter K. Jarrett, Trumbull, both of Conn.; David W. Wang, Vestal, N.Y.

[73] Assignee: American Cyanamid Company, Stamford, Conn.

[21] Appl. No.: 900,957

[22] Filed: Aug. 27, 1986

[51] Int. Cl.⁴ .............................................. A61F 5/04
[52] U.S. Cl. ......................... 128/92 YP; 128/92 YR; 623/16
[58] Field of Search ............... 128/92 YR, 92 YP; 623/16

[56] References Cited

U.S. PATENT DOCUMENTS

| | | | |
|---|---|---|---|
| 4,338,926 | 7/1982 | Kummer et al. | 623/16 |
| 4,365,356 | 12/1982 | Broemer et al. | 623/16 |
| 4,512,038 | 4/1985 | Alexander et al. | 128/92 XP |
| 4,550,449 | 11/1985 | Tunc | 128/92 YR |
| 4,605,415 | 8/1986 | Richez | 623/16 |
| 4,610,692 | 9/1986 | Eitenmuller et al. | 623/16 |
| 4,636,526 | 1/1987 | Dorrim et al. | 623/16 |
| 4,655,777 | 4/1987 | Dunn et al. | 623/16 |

FOREIGN PATENT DOCUMENTS

| | | | |
|---|---|---|---|
| 0146398 | 6/1985 | European Pat. Off. | 128/92 YR |
| 0011528 | 5/1980 | France | 128/92 YR |

OTHER PUBLICATIONS

*The Merck Index* Tenth Ed., p. 7439, 1983, Windholz et al.
*The Condensed Chemical Dictionary*, Tenth edition, Hawley, 1981, pp. 830–832.

Primary Examiner—C. Fred Rosenbaum
Assistant Examiner—Mark F. Colosimo
Attorney, Agent, or Firm—David A. Warmbold; Charles F. Costello, Jr.

[57] ABSTRACT

A bone fixation device is disclosed. The device comprises an absorbable homopolymer of 1-lactide or dl-lactide, or a copolymer of 1-lactide, and a reinforcement material. The reinforcement material can be a particulate filler of hydroxyapatite or a plurality of alumina fibers.

14 Claims, 4 Drawing Sheets

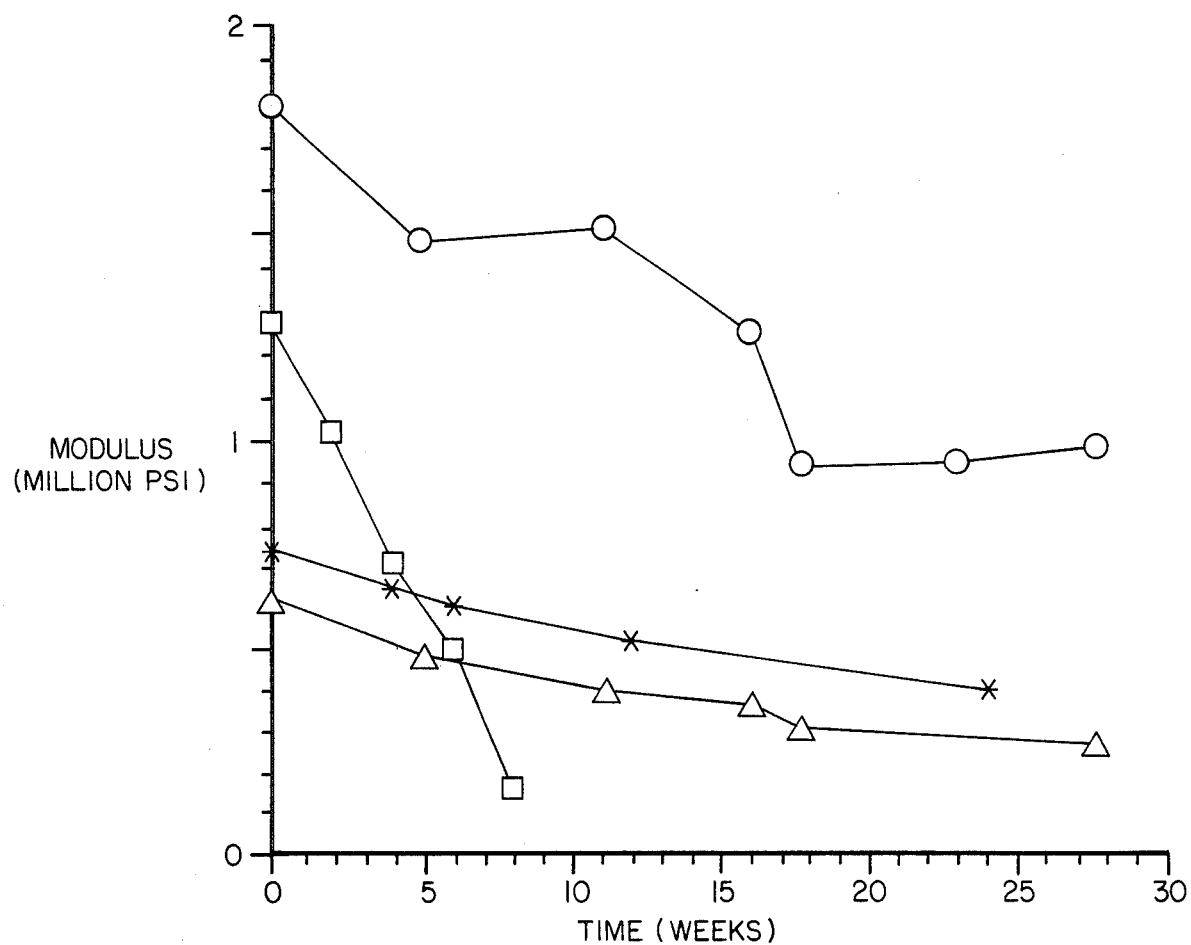

FIG. 1

FLEXURAL MODULUS DEGRADATION IN VIVO

○ COMPOSITE FROM EXAMPLE 1 [POLY(ℓ-LACTIDE)η INHERENT (0.5 g/dℓ IN CHCl₃):
   2.68 dℓ/g, REINFORCED WITH ALUMINA FABRIC].

△ POLY(ℓ-LACTIDE) OF EXAMPLE 1.

□ COMPOSITE OF POLY(dℓ-LACTIDE), REINFORCED WITH ALUMINA FIBER
   (IN VITRO DATA FROM: T.R. TICE, et.al. "BIODEGRADATION OF MICROCAPSULES
   AND BIOMEDICAL DEVICES PREPARED WITH RESORBABLE POLYESTERS."
   9th INTERNATIONAL SYMPOSIUM ON CONTROLLED RELEASE OF BIOACTIVE
   MATERIALS, 21ff, 1982).

✳ HIGH MOLECULAR WEIGHT POLY(ℓ-LACTIDE) [η] (CHCl₃) = 7.14 dℓ/g.
   (IN VIVO DATA FROM: EUROPEAN PATENT APPLICATION 108,635).

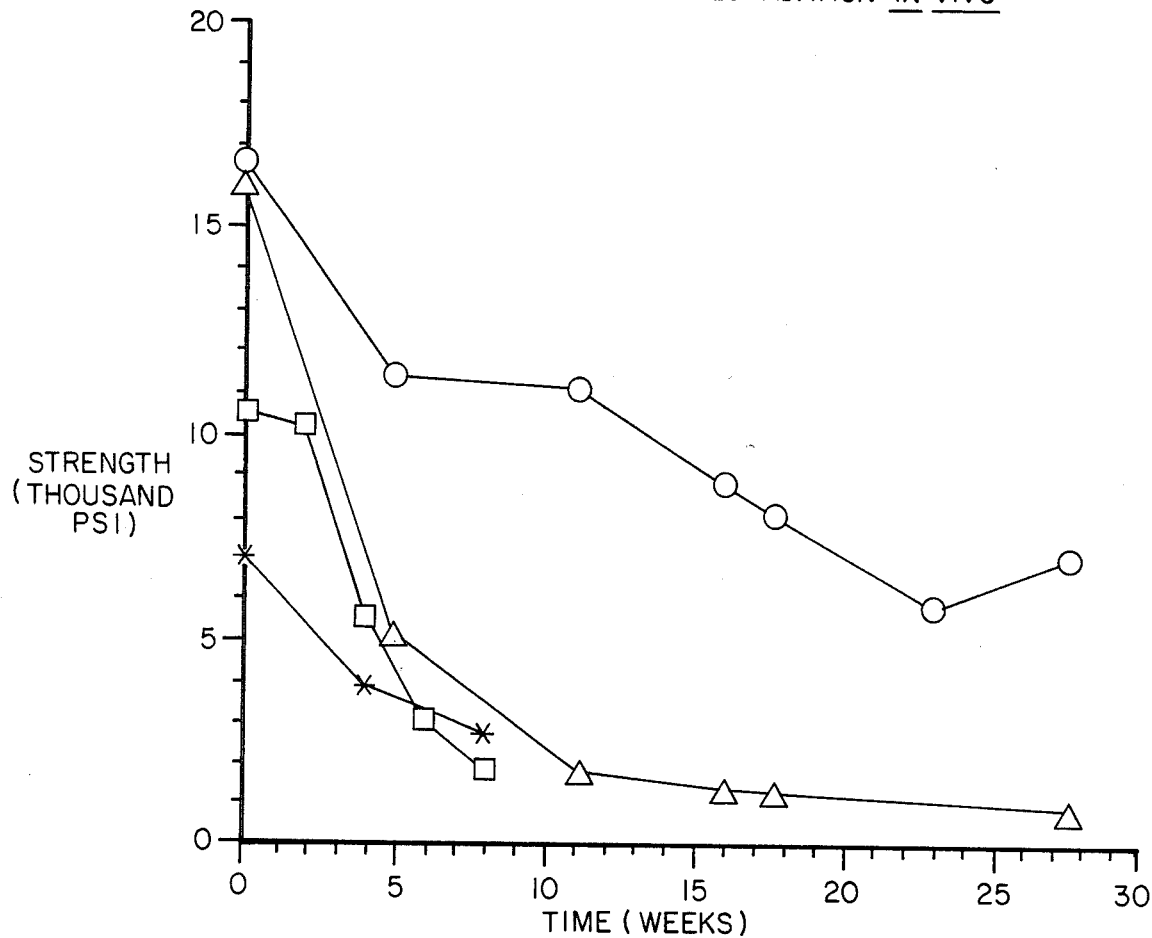

FIG. 2

FLEXURAL STRENGTH DEGRADATION IN VIVO

○ COMPOSITE FROM EXAMPLE 1 [POLY(ℓ-LACTIDE) $\eta$ INHERENT (0.5g/dℓ IN CHCl$_3$): 2.68 dℓ/g, REINFORCED WITH ALUMINA FABRIC].

△ POLY(ℓ-LACTIDE) OF EXAMPLE 1.

□ COMPOSITE OF POLY(dℓ-LACTIDE), REINFORCED WITH ALUMINA FIBER (IN VITRO DATA FROM: T.R. TICE, et.al. "BIODEGRADATION OF MICROCAPSULES AND BIOMEDICAL DEVICES PREPARED WITH RESORBABLE POLYESTERS," 9th INTERNATIONAL SYMPOSIUM ON CONTROLLED RELEASE OF BIOACTIVE MATERIALS, 21ff, 1982).

∗ HIGH MOLECULAR WEIGHT POLY(ℓ-LACTIDE) [$\eta$] (CHCl$_3$) = 7.14 dℓ/g. (IN VIVO DATA FROM: EUROPEAN PATENT APPLICATION 108,635).

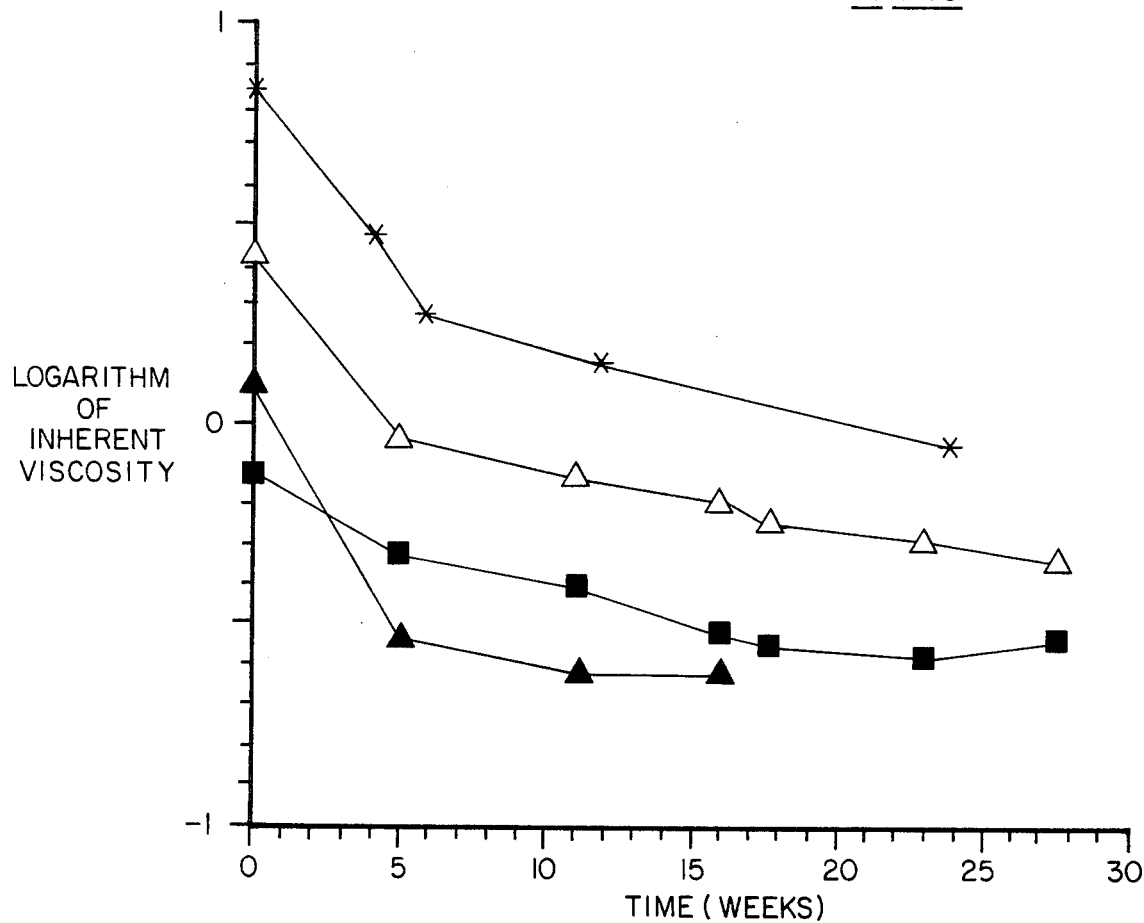

FIG. 3

MOLECULAR WEIGHT DEGRADATION IN VIVO

✽ POLY($l$-LACTIDE) - INITIAL $[\eta]$ (CHCl$_3$) = 7.14 d$l$/g
  (INTRINSIC VISCOSITY DATA FROM: EUROPEAN PATENT APPLICATION 108,635).

△ POLY($l$-LACTIDE) AS USED IN EXAMPLES 1 AND 2 - INITIAL $\eta$ INHERENT (0.5 g/d$l$ IN CHCl$_3$ = 2.68 d$l$/g.

■ POLY($l$-LACTIDE)(SIMILAR TO THE POLYMER USED IN EXAMPLES 1 AND 2)- INITIAL $\eta$ INHERENT (0.5 g/d$l$ IN CHCl$_3$) = 0.74 d$l$/g ▲ POLY(d$l$-LACTIDE) AS USED IN EXAMPLE 13 - INITIAL $\eta$ INHERENT (0.5 g/d$l$ IN CHCl$_3$) = 1.28 d$l$/g.

SURGICAL PROSTHESIS

BACKGROUND OF THE INVENTION

This invention relates to surgical structural elements consisting of bioabsorbable or semi-bioabsorbable composites, as well as to products and applications using these materials. Such surgical structural devices may include plates, screws, nails, pegs, rods, pins and any other device which would require a bioabsorbable material with relatively high rigidity and strength.

The use of internal bone fixation is an established and clinically used technique. The two major types of internal fixation devices are bone plates and intramedullary rods. The particular form intended for this invention is as an internal bone fixation plate.

Bone plates are applicable to a large variety of bones including load bearing as well as non-load bearing bones. Presently, more long bone fixations are done with intramedullary rods. Both of these devices are traditionally made of metal, e.g. stainless steel 316. There are two major disadvantages, however, associated with the presently used metal plates:

(1) Metal plates have a modulus approximately one order of magnitude greater than cortical bone. This mismatch in stiffness is known to cause stress protection induced osteoporosis or osteopenia. The increase in porosity and decrease in cortical wall thickness results in a weakened bone which is prone to refracture once the bone plate is removed.

(2) The metal plates must be removed due to their non-biodegradable nature coupled with the eventual possibility of corrosion. A second surgical procedure is therefore required which may introduce further complications.

The use of lower stiffness materials such as non-absorbable composites and tubular steel have been investigated. However, no human trials of these materials are known.

Lower stiffness bone fixation devices have advantages over metal plates. For example the stiffness of a bone plate can be made essentially equal to the modulus of cortical bone. If the low stiffness bone plate is also bioabsorbable, it does not have to be surgically removed. Thus the need for a second surgical procedure is eliminated.

Considerable research has therefore been devoted to the development of low stiffness bone plate materials. The properties which are most desirable in a bone plate are:

(1) The bone plate should provide a firm fixation of the broken bone to promote union during the early stages of healing.

(2) Once union has occurred, the load which was initially supported by the bone plate, would be gradually transferred back to the bone. This would induce the formation of stronger more dense bone at the fracture site thus accelerating the healing process.

(3) After the bone heals (3 to 6 months after implantation) the bone plate would completely lose its ability to support a load. The bone would then be once again subjected to its normal stresses.

Bioabsorbable materials with an initial modulus and strength at or near those of cortical bone are useful as internal bone fracture fixation devices for load bearing as well as non-load bearing bones.

The completely bioabsorbable or semi-absorbable composites of this invention are superior in mechanical properties and in biological behavior to the stainless steel devices presently used. The mechanical properties of these composites can be tailored to the specific end-use application. The devices of this invention will gradually lose their mechanical properties and will ultimately fully or partially disappear.

PRIOR ART

U.S. Pat. Nos. 4,411,027 and 4,329,743 disclose laminates composed of carbon fiber in a poly (lactic acid) (PLA) matrix. These are multiple layer laminates consisting of unidirectional continuous fiber-reinforced PLA plies or random chopped fiber reinforced plies. The stiffness and strength properties of this material appeared to be high for bone plate use (application as a ligament replacement and tissue scaffold was the primary use reported). The material appeared to degrade rapidly, although after 8 weeks in vivo the mechanical properties were still well above those of bone. The cited patents do not specify what stereoisomeric form or molecular weight of poly(lactic acid) (PLA) is used.

U.S. Pat. No. 4,279,249 discloses a bone fixation plate consisting of poly(1-lactide) reinforced with poly(glycolic acid) fibers. A similar composite, described in P. Cristel et al. "Biodegradable Composites For Internal Fixation" Biomaterials 3 271 (1982), has a low modulus relative to human cortical bone.

Composites of poly(dl-lactide) with calcium meta phosphate, tricalcium phosphate and calcium aluminate fibers are disclosed in European patent application No. 146,398.

European patent application No. 108,635 discloses the use of very high molecular weight poly(1-lactide) without reinforcement as a bone plate. A bone plate made with only poly(1- lactide) has to be relatively thick (plates used on dogs were 1 cm thick) to provide adequate stiffness and strength. A bending modulus of 740,000 psi and an ultimate strength at 8,300 psi were reported.

T. R. Tice et al. "Biodegradation of Microcapsules and Biomedical Devices Prepared with Resorbable Polyesters", 9th International Symposium on Controlled Release of Bioactive Materials, 21ff (1982) disclose data on poly(dllactide) reinforced with a high modulus fiber. The fibers used were graphite (Thornel TM, Union Carbide Company, Conn., U.S.A.); ceramic (Nextel TM, 3-M Company, Minn., U.S.A.), and alumina (Fiber FP TM, DuPont Company, Del., U.S.A.). The principal application of the device is stated to be mandibular fractures. The time span of useful properties in all devices studied is much too short (nearly complete loss of mechanical properties in less than two months exposure in saline solution) for use in long bone fixation. The poly(dl-lactide) matrix polymers are described as low molecular weight (initial inherent viscosity 0.7 dl/g in $CHCl_3$ 0.5 g/dl) and high molecular weight (initial inherent viscosity 0.8–0.95 dl/g in $CHCl_3$, 0.5 g/dl). These polymers have appreciably lower viscosities than the poly(1-lactide) used in our alumina composite (inherent viscosity 2.68 in $CHCl_3$, 0.5 g/dl). Fiber loadings in the Tice, et al poly(dl-lactide) composites were not described.

All of the above discussed prior art references are incorporated herein by reference.

The choice of particular materials for use in an absorbable or semi-absorbable bone fixation device is dependent in part upon the mechanical properties of the materials, since it is desired that the initial mechanical properties be similar to bone. In addition, the behavior of the materials in the physiological environment, i.e. bioabsorption rate and tissue response, are of equal importance.

None of the unreinforced bioabsorbable materials tested had the required modulus or strength. These included poly(l-lactide), poly(dl-lactide), poly(glycolide), and copolymers of lactide and glycolide. It was found, however, that composites of a bioabsorbable polymer with a high stiffness fiber reinforcement, such as alumina fiber, provided acceptable properties.

The choice of a polymer to use as a matrix in a fiber reinforced composite was dependent in part upon its mechanical properties, but more emphasis was given to its in vivo behavior. Poly(l-lactide) has advantages over the other polymers evaluated. Poly(glycolide) was judged to be inadequate due to its rapid absorption rate, which would not allow it to meet the reqired service period. Poly(dl-lactide) is an amorphous material. The lack of crystallinity not only makes it a weaker polymer than poly(l-lactide), but also causes very different in vivo behavior. Poly(dl-lactide) imbibes moisture at a much faster rate than Poly (l-lactide); this causes both plasticization and distortion of the implant over a relatively short period (less than 1 month). It also results in a much faster degradation rate than would be acceptable for long bone fixation. In addition, noncrystalline poly(dl-lactide) is subject to creep under load bearing condition, especially when plasticized by body fluids. Poly (dl-lactide) as also found to be more difficult to machine when the temperature of the material is increased to above $T_g$, due to the heat generated by friction. The problems cited for poly(dl-lactide) were also found to be true for copolymers of l-lactide and glycolide, although properties improved with higher l-lactide content. This is due to the corresponding increase in crystallinity of the higher l-lactide copolymers. Pure poly(l-lactide) was found to perform well with respect to the abovementioned criteria. For these reasons, poly(l-lactide) was chosen as the preferred matrix material.

The molecular weight of the poly(l-lactide) matrix was also found to be an important factor. The use of a high molecular weight material would be preferred to assure our strength retention criteria are met. On the other hand, it was found that lower molecular weight polymer provided a composite with better mechanical properties. It was for this reason that the intermediate inherent viscosity range of 1.5 to 3.5 dl/g (0.5 g/dl in $CHCl_3$) was selected.

SUMMARY OF THE INVENTION

A bioabsorbable device with an adjustable initial modulus which can be set at, above or below the modulus of bone, and which loses properties at a controllable, predictable rate after implantation has been invented. The device may consist of a poly(l-lactide) matrix reinforced with α-alumina fibers (DuPont Fiber FP TM) or aramid fibers (DuPont Kevlar TM), or it may consist of a high molecular weight poly(dl-lactide) matrix reinforced with ultra high modulus polyethylene fibers (Allied A-900 TM, Allied Corp., N.J., U.S.A. These three composite systems are examples of semi-adsorbable surgical devices.

This invention uses a combination of materials which may consist of a bioabsorbable polymer and a reinforcement fiber (which may or may not be bioabsorbable), or a bioabsorbable polymer and a bioabsorbable filler. The component materials are combined in such a way as to have bending, axial and torsional stiffness and strength suitable for the biomechanical demands placed upon it. The material will, subsequent to implantation, gradually lose both stiffness and strength according to the time frame for which useful properties are required. The material will ultimately be completely or partially absorbed by the body, any residue being both inert in the body and beneft of significant mechanical properties. No surgical procedure to remove the device would be required.

A bone fixation device has been invented. The device comprises an absorbable polymer and the polymer is obtained from the polymerization of l-lactide, and a reinforcement material.

In one embodiment, the polymer is obtained from the copolymerization of l-lactide and dl-lactide. In another embodiment the polymer is obtained from the copolymerization of l-lactide and glycolide. In a further embodiment, the polymer is obtained from the copolymerization of l-lactide and 1,3-dioxan-2-one.

In yet another embodiment, and in combination with any of the above embodiments, the reinforcement material is a filler. In a specific embodiment, the filler is in particulate form. In a more specific embodiment, the particulate filler is hydroxyapatite. In another specific embodiment, the filler is selected from the group consisting of tricalcium phosphate, hydroxyapatite, and a mixture thereof.

In a still further embodiment, and in combination with any of the above polymer embodiments, the reinforcement material is manufactured from a plurality of fibers. The fiber material is selected from the group consisting of alumina, poly (p-phenylene terephthalamide), polyethylene terephthalate, and ultra high modulus polyethylene. In a specific embodiment the fiber is poly(p-phenylene terephthalamide. In another specific embodiment, the fiber is polyethylene terephthalate. In a further specific embodiment, the fiber is alumina.

In a more specific embodiment, the fiber is alpha alumina.

An alternative bone fixation device has been invented. The alternative device comprises an absorbable polymer and a reinforcement material manufactured from a plurality of ultra high modulus polyethylene fibers. The absorbable polymer is obtained from the polymerization of dl-lactide.

Another alternative bone fixation device has been invented. The device comprises an absorbable polymer, said polymer obtained from the copolymerization of l-lactide, dl-lactide, and a monomer selected from the group consisting of glycolide, 1,3-dioxan-2-one, and p-dioxanone and a reinforcement material. In one embodiment, the monomer is glycolide. In another embodiment, the monomer is 1,3-dioxan-2-one.

In yet another embodiment, and in combination with any of the above alternative bone fixation device embodiments, the reinforcement material is a filler. In a specific embodiment, the filler is in particulate form. In a more specific embodiment, the particulate filler is hydroxyapatite. In another specific embodiment, the filler is selected from the group consisting of tricalcium phosphate, hydroxyapatite, and a mixture thereof.

In a still further embodiment, and in combination with any of the above (alternative device) polymer embodiments, the reinforcement material is manufactured from a plurality of fibers selected from the group consisting of alumina, poly(p-phenylene terephthalamide), polyethylene terephthalate, and ultra high modulus polyethylene. In a specific embodiment, the fiber is alumina. In a more specific embodiment, the fiber is alpha alumina.

A laminated bone fixation device has also been invented. The device comprises an impregnating agent consisting of an absorbable polymer matrix. The polymer is obtained from the polymerization of 1-lactide. The matrix has an inherent viscosity of about 1.5 to 3.5 dl/g (0.5 g/dl in $CHCl_3$). The device also comprises a nonabsorbable reinforcement material. The reinforcement material consists essentially of at least one alumina fiber. The device has a flexural strength of about 10,000 to 25,000 psi; a flexural modulus of about $1 \times 10^6$ to $5 \times 10^6$ psi; a loss of about 30% of initial flexural strength during 3 months in vivo and 60% during 6 months in vivo; and a loss of about 25% of initial flexural modulus during 3 months in vivo and 45% during 6 months in vivo.

In one embodiment, the reinforcement material is a plurality of alpha alumina fibers. In a specific embodiment, the reinforcement material comprises about 10 to 60 volume percent of said fibers. In a more specific embodiment, the device comprises about 15 to 40 percent of said fibers. In another embodiment, the device has a flexural strength of about 15,000 to 25,000 psi. In a further embodiment, the device has a flexural modulus of up to about $3 \times 10^6$ psi.

BRIEF DESCRIPTION OF THE DRAWINGS

FIG. 1 is a graph showing the in vivo flexural modulus degradation of the device of this invention, as contrasted with the moduli of prior art bone fixation devices;

FIGS. 2 and 3 are graphs, similar to that of FIG. 1, showing in vivo flexural strength and molecular weight degradation, respectively;

DESCRIPTION OF THE PREFERRED EMBODIMENTS

The following is a description for making the composite materials used in the bone fixation device of this invention.

1. Bioabsorbable Particulate Filled Systems (A) A monomer or monomer mixture is polymerized in bulk in a stirred reactor under nitrogen or vacuum. When the polymer melt viscosity reaches a maximum the particulate filler is added slowly to the concentration desired.

(B) A bioabsorbable matrix polymer is heated to melting under nitrogen or vacuum in a mixing chamber. To the melt, the particulate filler (tricalcium phosphate or hydroxyapatite) is added slowly until thorough mixing is observed at the desired concentration.

2. Fiber Reinforced Systems (A) Solution Impregnation and Laminations:

The fiber or woven fabric is immersed in a solution of the biodegradable polymer in a low boiling point solvent (e.g. methylene chloride). The amount of polymer deposited on the fabric, chopped fiber or fiber yarn is dependent on the solution concentration, the polymer molecular weight (which effects solution viscosity), the length of immersion time and the number of immersions. The impregnated chopped fiber, yarn or fabric (prepreg) is then thoroughly dried. The prepreg is laid-up in a mold of a predetermined thickness. Vacuum is applied to the lay-up by use of a vacuum bag. Heat and compression are then applied to consolidate the laminate.

(B) Melt Impregnation and Lamination:

Films of the biodegradable polymer are made by solvent casting or melt pressing. Alternatively, fibrous mats are made from polymer by running a solution of the polymer into a non-solvent in a thin stream to form a stringy precipitate, followed by pressing into a mat at room temperature. The films or mats are then laid between yarn or fabric layers in a mold of a predetermined thickness. Vacuum is applied to the lay-up, by vacuum-bagging the mold, and heat and compression are applied to consolidate the laminate.

Figure 4:
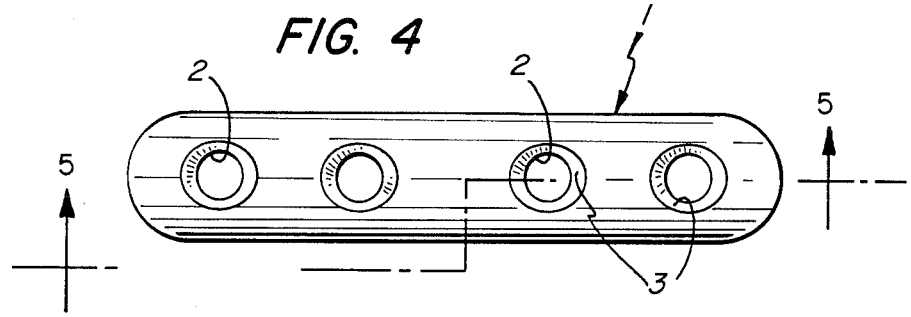
FIG. 4 is a top view of a bone fixation device manufactured from the composite materials of this invention.
Figure 6:
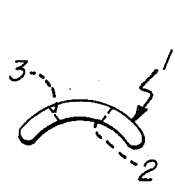
FIG. 6 is a front view of FIG. 5.
Figure 5:
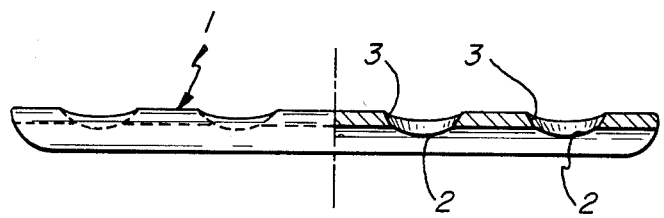
FIG. 5 is a partially broken side view of FIG. 4.

FIGS. 4 to 6 show the bone fixation device. The device can be manufactured without undue experimentation by methods known in the prior art, e.g. by compression molding. The device can be attached to a bone by any means presently known or obvious to a person having ordinary skill in the art, for example by fastening with screws, staples and the like, or by bonding, for example, by gluing the device to the bone.

Figure 7:
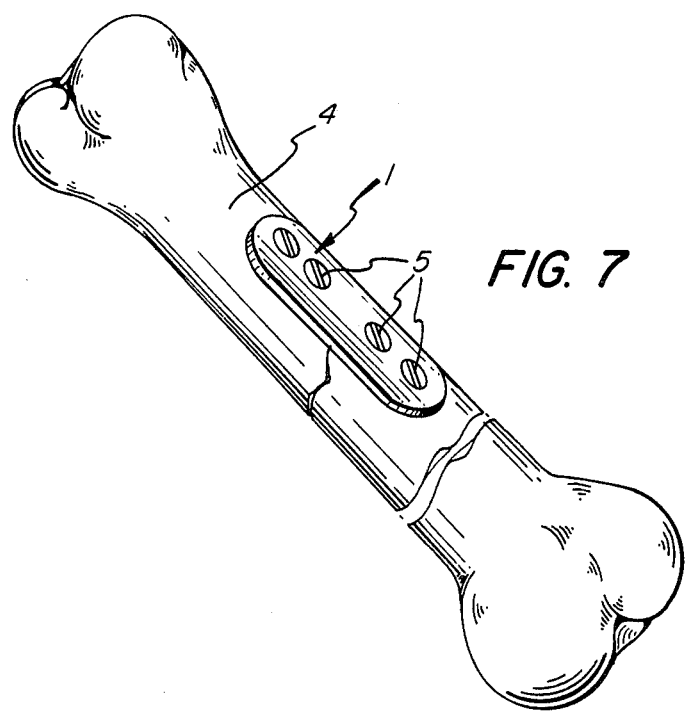
FIG. 7 is a broken perspective view of FIGS. 4 to 6 showing the use of the device on a mammalian bone.

FIGS. 4 to 6 show holes 2 which are used to each accommodate a screw 5 (shown in FIG. 7). To accommodate the screw head, a plurality of holes 2 are countersunk 3 in the device 1.

Referring specifically to FIGS. 4 and 5, four holes 2 are shown. It is to be understood that any number of holes can be used, provided the device 1 is adequately attached to a bone 4 (shown in FIG. 7). However, as a minimum, at least two holes 2 and screws 5 appear to be necessary.

Referring to FIG. 7, the preferred relationship of the device 1 to a mammalian bone 4 fracture is shown. Under many circumstances, the configuration shown in FIG. 7 will allow the best possible chance for uniform healing of the fracture in the bone 4.

The following examples more fully describe the above embodiments.

EXAMPLE 1

Poly(l-lactide)-Alumina Fiber Laminate:

The laminate was formed from poly(l-lactide) of inherent viscosity 2.68 dl/g (0.5 g/dl in $CHCl_3$, after consolidation) and a fabric made from alumina fiber. Poly(1-lactide) was melt pressed into 4" by 4" square films, two films of 0.005" and two films of 0.023" thickness. The laminate was formed by stacking the films and fabric in alternating layers. Three plies of fabric were used. The 0.005" thick films were used for the two outside layers. The laminate was consolidated by heating to 200° C. in a vacuum bag and compressing to a thickness of 1/16". The laminate contained 19% alumina fabric by volume. The laminate had the following mechanical properties:

FLEXURAL MODULUS $1.81 \times 10^6$ psi
FLEXURAL STRENGTH $16.6 \times 10^3$ psi This material is of particular interest due to its superior in vivo performance in subcutaneous rabbit implant experiments. The degradation of this material in vivo is shown in FIGS. 1–3. FIGS. 1 and 2 show the physical property degradation profile and FIG. 3 shows the molecular weight degradation profile, as contrasted with materials used in prior art bone fixation devices. The initial properties of this composite system can be varied over a wide range by varying fiber loading. In addition, the degradation profile can be altered by varying the initial molecular weight of the matrix polymer.

Mechanical properties declined in a roughly linear manner over a 6 month period in rabbits to a level at 39% of initial flexural strength and 53% of initial flexural modulus. Inherent viscosity data suggest that mass loss of the poly(l-lactide) matrix would begin after approximately 42 weeks. After mass loss onset, the rate of mechanical property degradation should increase and any remaining load bearing capability would quickly deteriorate.

EXAMPLE 2

Poly(l-lactide)-Kevlar Laminate:

A laminate was formed which consisted of a poly(l-lactide) of inherent viscosity 1.00 dl/g (0.5 g/dl in CHCl$_3$, before consolidation) and a satin weave Kevlar 49 fabric. The polymer was dissolved in methylene chloride at a concentration of 5% (w/v). Kevlar fabric was immersed in the solution to form a prepreg of 22% poly(l-lactide) by weight. Poly(l-lactide) was melt pressed into films approximately 0.004" thick. Seven polymer films and six plies of prepreg were laid-up in alternating layers. The laminate was consolidated by heating at 200° C. in a vacuum bag and compressing to a thickness of 1/16". The resulting laminate was 49% Kevlar by volume. The laminate had the following mechanical properties:
FLEXURAL MODULUS $2.17 \times 10^6$ psi
FLEXURAL STRENGTH $24.2 \times 10^3$ psi

EXAMPLE 3

Poly(l-lactide)-Alumina Laminate:

A laminate was formed which consisted of a poly(l-lactide) of inherent viscosity 1.64 dl/g (0.5 g/dl in CHCl$_3$, after consolidation) and a fabric made from alumina fiber. Poly(l-lactide) was reprecipitated from a chloroform solution into methanol. The dried precipitate was pressed into 4" by 4" square mats, two mats of 6.5 g and two mats of 1.2 g. The laminate was formed by stacking the mats and fabric in alternating layers. Three plies of fabric were used. The 1.2 g mats were used for the two outside layers. The laminate was consolidated by heating to 195° C. in a vacuum bag and compressing to a thickness of 1/16". The laminate contained 17% alumina fabric by volume. The laminate had the following mechanical properties:
FLEXURAL MODULUS $1.81 \times 10^6$ psi
FLEXURAL STRENGTH $19.9 \times 10^3$ psi

EXAMPLE 4

Poly(l-lactide)-Alumina Laminate:

A laminate was formed which consisted of a poly(l-lactide) of inherent viscosity 2.65 dl/g (0.5 g/dl in CHCl$_3$, after consolidation) and a fabric made from alumina fiber. Poly(l-lactide) was reprecipitated from a chloroform solution into methanol. The dried precipitate was pressed into 4" by 4" square mats, two mats of 6.5 g and two mats of 1.2 g. The laminate was formed by stacking the mats and fabric in alternating layers. Three plies of fabric were used. The 1.2 g mats were used for the two outside layers. The laminate was consolidated by heating to 195° C. in a vacuum bag and compressing to a thickness of 1/16". The laminate contained 17% alumina fabric by volume. The laminate had the following mechanical properties:
FLEXURAL MODULUS $1.52 \times 10^6$ psi
FLEXURAL STRENGTH $16.5 \times 10^3$ psi

EXAMPLE 5

Poly(l-lactide)-Alumina Laminate:

A laminate was formed which consisted of a poly(l-lactide) of inherent viscosity 4.14 dl/g (0.5 g/dl in CHCl$_3$, after consolidation) and a fabric made from alumina fiber. Poly(l-lactide) was reprecipitated from a chloroform solution into methanol. The dried precipitate was pressed into 4" by 4" square mats, two mats of 6.5 g and two mats of 1.2 g. The laminate was formed by stacking the mats and fabric in alternating layers. Three plies of fabric were used. The 1.2 g mats were used for the two outside layers. The laminate was consolidated by heating to 195° C. in a vacuum bag and compressing to a thickness of 1/16". The laminate contained 17% alumina fabric by volume. The laminate had the following mechanical properties:
FLEXURAL MODULUS $1.46 \times 10^6$ psi
FLEXURAL STRENGTH $15.0 \times 10^3$ psi A summary of the flexural strength and flexural modulus data for Examples 3 to 5 is contained in the following Table.

TABLE I

Accelerated In Vitro Degradation
Effect Of Initial Polymer Molecular Weight: Alumina-Poly(l-lactide) Composites

| Composite From Example | Initial $\eta^{inh}$ (CHCl$_3$) | Flexural Strength (psi) $\times 10^{-3}$ Days | | | | | | Flexural Modulus (psi) $\times 10^{-6}$ Days | | | | | |
|---|---|---|---|---|---|---|---|---|---|---|---|---|---|
| | | (0) | (2) | (5) | (8) | (12) | (19) | (0) | (2) | (5) | (8) | (12) | (19) |
| Non-Sterile Samples | | | | | | | | | | | | | |
| 3 | 1.64 | 19.9 | 15.6 | 9.60 | 6.90 | 4.35 | 2.35 | 1.81 | 1.38 | 1.03 | 0.78 | 0.71 | 0.42 |
| 4 | 2.65 | 16.5 | 9.45 | 7.70 | 5.10 | 2.16 | 2.03 | 1.52 | 0.63 | 1.01 | 0.79 | 0.35 | 0.27 |
| 5 | 4.14 | 15.0 | 10.9 | 8.00 | 6.50 | 4.40 | 2.62 | 1.46 | 0.95 | 0.79 | 1.00 | 0.66 | 0.34 |
| Ethylene Oxide Sterilized | | | | | | | | | | | | | |
| 3 | 1.64 | 20.9 | 14.1 | 9.27 | — | — | — | 1.96 | 1.45 | 0.90 | — | — | — |
| 4 | 2.65 | 17.3 | 6.30 | 7.70 | — | — | — | 1.70 | 0.90 | 1.14 | — | — | — |
| 5 | 4.14 | 15.9 | 12.1 | 11.3 | — | — | — | 1.45 | 1.26 | 1.34 | — | — | — |
| Gamma Radiation Sterilized (2.5 mrad) | | | | | | | | | | | | | |
| 3 | 1.64 | 18.5 | 9.40 | 6.60 | — | — | — | 2.17 | 1.09 | 0.95 | — | — | — |
| 4 | 2.65 | 13.5 | 11.80 | 4.34 | — | — | — | 1.41 | 1.36 | 0.85 | — | — | — |
| 5 | 4.14 | 13.2 | 7.34 | 3.40 | — | — | — | 1.74 | 0.81 | 0.64 | — | — | — | the two outside layers. The laminate was consolidated by heating to 195° C. in a vacuum bag and compressing to a thickness of 1/16". The laminate contained 17%

EXAMPLE 6

Poly(l-lactide)-Alumina Laminate:

A laminate was formed which consisted of a poly(l-lactide) of inherent viscosity 2.64 dl/g (0.5 g/dl in CHCl$_3$, before consolidation) and a fabric made from alumina fiber. Poly(l-lactide) was melt pressed into 4" by 4" square films, two films of 0.005" and one film of 0.045" thickness. The laminate was formed by stacking the films and fabric in alternating layers. Two plies of fabric were used. The 0.005" films were used for the two outside layers. The laminate was consolidated by heating to 200° C. in a vacuum bag and compressing to a thickness of 1/16". The laminate contained 13% alumina fabric by volume. The laminate had the following mechanical properties:
FLEXURAL MODULUS 2.09×10$^6$ psi
FLEXURAL STRENGTH 17.7×10$^3$ psi CHCl$_3$, before consolidation) and a fabric made from alumina fiber. Poly(l-lactide) was melt pressed into 4" by 4" square films, two films of 0.005" and four films of 0.008" thickness. The laminate was formed by stacking the films and fabric in alternating layers. Five plies of fabric were used. The 0.005" films were used for the two outside layers. The laminate was consolidated by heating to 200° C. in a vacuum bag and compressing to a thickness of 1/16". The laminate contained 30% alumina fabric by volume. The laminate had the following mechanical properties:
FLEXURAL MODULUS 3.62×10$^6$ psi
FLEXURAL STRENGTH 24.1×10$^3$ psi A summary of the flexural strength and flexural modulus data for Examples 6 to 9 is contained in the following Table.

TABLE II

Accelerated In Vitro Degradation
Effect of Fiber Loading: Alumina-Poly(l-lactide) Composites

| Composite From Example | Alumina Fiber Volume % | Flexural Strength (psi) × 10$^{-3}$ Days | | | Flexural Modulus (psi) × 10$^{-6}$ Days | | |
|---|---|---|---|---|---|---|---|
| | | (0) | (2) | (5) | (0) | (2) | (5) |
| 6 | 13 | 17.7 | 5.87 | 3.45 | 2.09 | 0.95 | 0.76 |
| 7 | 19 | 17.7 | 8.60 | 4.67 | 1.90 | 1.04 | 0.89 |
| 8 | 24 | 21.6 | 11.1 | 8.17 | 2.94 | 1.57 | 1.36 |
| 9 | 30 | 24.1 | 10.7 | 8.76 | 3.62 | 1.46 | 1.34 |

EXAMPLE 7

Poly(l-lactide)-Alumina Laminate:

A laminate was formed which consisted of a poly(l-lactide) of inherent viscosity 2.64 dl/g (0.5 g/dl in CHCl$_3$, before consolidation) and a fabric made from alumina fiber. Poly(l-lactide) was melt pressed into 4" by 4" square films, two films of 0.005" and two films of 0.023" thickness. The laminate was formed by stacking the films and fabric in alternating layers. Three plies of fabric were used. The 0.005" films were used for the two outside layers. The laminate was consolidated by heating to 200° C. in a vacuum bag and compressing to a thickness of 1/16". The laminate contained 19% alumina fabric by volume. The laminate had the following mechanical properties:
FLEXURAL MODULUS 1.90×10$^6$ psi
FLEXURAL STRENGTH 17.7×10$^3$ psi

EXAMPLE 8

Poly(l-lactide)-Alumina Laminate:

A laminate was formed which consisted of a poly(l-lactide) of inherent viscosity 2.64 dl/g (0.5 g/dl in CHCl$_3$, before consolidation) and a fabric made from alumina fiber. Poly(l-lactide) was melt pressed into 4" by 4" square films, two films of 0.005" and three films of 0.015" thickness. The laminate was formed by stacking the films and fabric in alternating layers. Four plies of fabric were used. The 0.005" films were used for the two outside layers. The laminate was consolidated by heating to 200° C. in a vacuum bag and compressing to a thickness of 1/16". The laminate contained 24% alumina fabric by volume. The laminate had the following mechanical properties:
FLEXURAL MODULUS 2.94×10$^6$ psi
FLEXURAL STRENGTH 21.6×10$^3$ psi

EXAMPLE 9

Poly(l-lactide)-Alumina Laminate:

A laminate was formed which consisted of a poly(l-lactide) of inherent viscosity 2.64 dl/g (0.5 g/dl in

EXAMPLE 10

Poly(l-lactide)-Alumina Laminate:

A laminate was formed by impregnating ½" chopped alumina fiber with poly(l-lactide). The polymer had an inherent viscosity of 2.64 dl/g (0.5 g/dl in CHCl$_3$, before consolidation). The impregnation was accomplished by dissolving the polymer in chloroform (10 g/dl) followed by stirring in the chopped fiber. The mixture was then dried under vacuum to constant weight. The impregnated fiber was consolidated using vacuum and compression at 200° C., forming a laminate containing 30% alumina by volume. The laminate had the following mechanical properties:
FLEXURAL MODULUS 1.77×10$^6$ psi
FLEXURAL STRENGTH 15.3×10$^3$ psi

EXAMPLE 11

In Vitro Degradation of Poly(l-lactide)-Alumina Laminates:

An accelerated in vitro degradation test was used to assess the relative degradation rates of laminates made with poly(l-lactide)s of different molecular weights reinforced with alumina fabric. The in vitro procedure involved immersing the sample in a pH 6.09 phosphate buffered aqueous solution at 67° C. The samples were removed from the bath, dried and tested for mechanical properties using the ASTM D790 method. Samples from Examples 3, 4 and 5 were used in this study. The results are shown in Table I. These data indicate that the composite fabricated with the lower molecular weight polymer (Example 3) possessed higher initial mechanical properties than the composites made with higher molecular weight polymers. It also appeared to have less scatter in its degradation profile.

EXAMPLE 12

In Vitro Degradation of Poly(l-lactide)-Alumina Laminates:

An accelerated in vitro degradation test was used to assess the relative degradation rates of laminates made with poly(1-lactide) reinforced with different loadings of alumina fabric. The in vitro procedure was identical to that described in Example 11. Samples from Examples 6, 7, 8 and 9 were used in this study. The results are shown in Table II. These data indicate that the composites possessed higher initial mechanical properties as the fabric volume increased. This relationship allows the tailoring of a material to have the mechanical properties desirable for a specific application within a fairly broad range.

EXAMPLE 13

Poly(dl-lactide)-Polyethylene Laminate:

A laminate was constructed using Ultra High Modulus Polyethylene (UHMPE) and poly(dl-lactide). The UHMPE fiber was laid-up in unidirectional plies with 0°, 90° orientation. Between each ply, a 0.003" thick film (melt pressed) of poly(dl-lactide) was laid. A film of polymer was placed on the top and the bottom of the lay-up as well. The laminate was consolidated by heating to 120° C. in a vacuum bag and compressing to a thickness of 1/16". The laminate contained 41% UHMPE by volume. The laminate had the following mechanical properties:
FLEXURAL MODULUS $1.28 \times 10^6$ psi
FLEXURAL STRENGTH $12.5 \times 10^3$ psi

EXAMPLE 14

Poly(1-lactide)-Polyethylene Terephthalate Laminate:

Poly(1-lactide) with an initial inherent viscosity of 3.63 dl/g (0.5 g/dl in $CHCl_3$) was dissolved in $CHCl_3$/ethyl acetate (V/V 9/1), at a concentration of 10% (w/v). Polyethylene terephthalate fabric was impregnated by dipping in the solution to a coating level of ±50% by weight. Six plies of this prepreg were then consolidated in a heated hydraulic press at 180° C. for 3 minutes with about 1500 psi pressure. The resulting laminate had a flexural modulus of $0.43 \times 10^6$ psi.

EXAMPLE 15

Poly(1-lactide)-Hydroxyapatite Composite:

Poly(1-lactide) was prepared by charging 100 g of 1-lactide, 15.5 ul (0.01 mole %) lauryl alcohol and 15.6 mg (0.01 mole %) stannous chloride dihydrate into a stirred reactor at 200° C. When the power drain on the stirring motor reached a maximum, 45 g of hydroxyapatite ($Ca_{10}(OH)_2(PO_4)_6$, Mallinckrodt) was added. The composite was discharged after it appeared homogeneous (about 5 min.). The composite contained about 14% hydroxyapatite by volume. The flexural properties of a compression molded plaque were:
FLEXURAL MODULUS $0.79 \times 10^6$ psi
FLEXURAL STRENGTH $0.92 \times 10^3$ psi

We claim:

1. A bone fixation device comprising an absorbable polymer matrix, said matrix obtained from the polymerization of 1-lactide, and a reinforcement material being a filler in a particulate, non-fiber form being suspended throughout the matrix and being selected from the group consisting of tricalcium phosphate, hydroxyapatite, and a mixture thereof.

2. A device of claim 1 wherein the particulate filler is hydroxyapatite.

3. A semi-absorbable bone fixation device comprising an absorbable polymer, said polymer obtained from the polymerization of 1-lactide, and a nonabsorbable reinforcement material providing increased structural integrity to said bone fixation device and being manufactured from a plurality of fibers selected from the group consisting of alumina, poly(p-phenylene terephthalamide), polyethylene terephthalate and ultra high modulus polyethylene.

4. A device of claim 3 wherein the fiber is poly (p-phenylene terephthalamide).

5. A device of claim 3 wherein the fiber is polyethylene terephthalate.

6. A device of claim 3 wherein the fiber is alumina.

7. A device of claim 6 wherein the fiber is alpha alumina.

8. A semi-absorbable bone fixation device comprising an absorbable polymer, said polymer obtained from the polymerization of dl-lactide, and a non-absorbable reinforcement material manufactured from a plurality of ultra high modulus polyethylene fibers to increase the structural integrity of the bone fixation device, said device having a flexural strength of about 10,000 to 25,000 psi, and a flexural modulus of about $1 \times 10^6$ to $5 \times 10^6$ psi.

9. A semi-absorbable laminated bone fixation device comprising an impregnating agent consisting of an absorbable polymer matrix, said matrix obtained from the polymerization of 1-lactide and having an inherent viscosity of about 1.5 to 3.5 dl/g (0.5 g/dl in $CHCl_3$), and a nonabsorbable reinforcement material to provide increased structural integrity to the bone fixation device consisting essentially of at least one alumina fiber such that the bone fixation device has a matrix with sufficiently high molecular weight to provide the desired strength retention time and sufficiently low molecular weight to provide adequate strength and modulus, said device having a flexural strength of about 10,000 to 25,000 psi; a flexural modulus of about $1 \times 10^6$ to $5 \times 10^6$ psi; a loss of about 30% of its initial flexural strength during 3 months in vivo and 60% during 6 months in vivo; and a loss of about 25% of its initial flexural modulus during 3 months in vivo and 45% during 6 months in vivo.

10. A device of claim 9 wherein said reinforcement material is a plurality of alpha alumina fibers.

11. A device of claim 10 wherein the fibers comprise about 10 to 60 percent of the volume of said device.

12. A device of claim 10 wherein the fibers comprise about 15 to 40 percent of the volume of said device.

13. A device of claim 12 having a flexural strength of about 15,000 to 25,000 psi.

14. A device of claim 13 having a flexural modulus of up to about $3 \times 10^6$ psi.

* * * * *